United States Patent

Matsugi et al.

[11] Patent Number: 5,884,621
[45] Date of Patent: *Mar. 23, 1999

[54] DEVICE FOR ADMINISTERING POWDERY MEDICINE

[75] Inventors: Hideo Matsugi; Hiroyuki Kawabe; Yuji Makino; Yoshiki Suzuki; Takao Fujii, all of Tokyo, Japan

[73] Assignee: Teijin Limited, Osaka, Japan

[*] Notice: This patent issued on a continued prosecution application filed under 37 CFR 1.53(d), and is subject to the twenty year patent term provisions of 35 U.S.C. 154(a)(2).

[21] Appl. No.: 817,250

[22] PCT Filed: Jul. 25, 1996

[86] PCT No.: PCT/JP96/02097

§ 371 Date: Mar. 24, 1997

§ 102(e) Date: Mar. 24, 1997

[87] PCT Pub. No.: WO97/04826

PCT Pub. Date: Feb. 13, 1997

[30] Foreign Application Priority Data

Jul. 25, 1995 [JP] Japan ................................... 7-189002

[51] Int. Cl.⁶ .................... A61M 15/00; A61M 16/00; B05D 7/14; B65D 83/06
[52] U.S. Cl. .................... 128/203.15; 604/58; 222/189
[58] Field of Search .................... 128/203.15, 203.21; 222/202–204, 211, 633; 239/328, 349; 604/58

[56] References Cited

U.S. PATENT DOCUMENTS

| | | | |
|---|---|---|---|
| 263,451 | 8/1882 | Adams | 128/203.15 |
| 280,202 | 6/1883 | Mattson | 128/203.15 |
| 310,444 | 1/1885 | Kibele | 128/203.15 |
| 355,816 | 1/1887 | Goodwillie | 128/203.15 |
| 443,545 | 12/1890 | Rowland | 128/203.15 |
| 464,969 | 12/1891 | Ives | 128/203.15 |
| 482,407 | 9/1892 | Magee | 128/203.15 |
| 4,007,858 | 2/1977 | Shay | 222/193 |
| 4,091,966 | 5/1978 | Laauwe | 222/211 |
| 4,286,735 | 9/1981 | Sneider | 222/189 |
| 4,307,823 | 12/1981 | Heiss et al. | 222/633 |
| 4,730,751 | 3/1988 | Mackles et al. | 222/189 |

FOREIGN PATENT DOCUMENTS

| | | | |
|---|---|---|---|
| 56-68460 | 6/1981 | Japan | A61M 13/00 |
| 2-500172 | 1/1990 | Japan | A61M 13/00 |

OTHER PUBLICATIONS

International Search Report

*Primary Examiner*—Kimberly L. Asher
*Attorney, Agent, or Firm*—Sughrue, Mion, Zinn, Macpeak & Seas, PLLC

[57] ABSTRACT

A device for administering a powdery medicine satisfying the requirements of portability, easy and quick operation, fabrication through simple steps, rigid structure, and economy using decreased number of parts of low cost. The device for administering a powdery medicine comprises a medicine-holding portion having at least partly flexible wall portion for defining therein a powdery medicine-container space which also serves as an air reservoir, and a medicine guide portion through which the space in said medicine-holding portion is communicated with the outside, wherein the space in said medicine-holding portion is communicated with the outside through said medicine guide portion only, said medicine guide portion is of a tubular structure having, at one end thereof, a medicine spray port at a position on the outside of said medicine-holding portion and having, at the other end thereof, a medicine suction port at a position in the space in said medicine-holding portion, the bottom of the space in said medicine-holding portion is positioned nearly just under the medicine suction port of said medicine guide portion, said medicine suction port is disposed close to said bottom, and the powdery medicine is sprayed to the outside through said medicine guide portion by depressing and relaxing the flexible wall portion of said medicine-holding portion.

19 Claims, 5 Drawing Sheets

Fig. 7 ial, as well as specifications thereof.

DEVICE FOR ADMINISTERING POWDERY MEDICINE

This application is a 371 of PCT/JP96/02097 filed Jul. 25, 1996.

TECHNICAL FIELD

The present invention relates to a device for administering a powdery medicine. More specifically, the invention relates to a device for administering a powdery medicine which is convenient to carry, easy to use, disposable after the use and is sanitary, rigid in construction, and is relatively cheaply available, the device holding in a container a trace amount of a powdery medicine for one-time administration into body cavities or to another diseased part by spray- or suction-administration.

BACKGROUND ART

Patients suffering from nasal allergy, asthma, flat lichen, wide inflammatory stomatitis and the like diseases are treated by administering powdery medicines into the nasal cavities or the oral cavity. The medicines are administered by using powdery medicine dispensers or containers. Such dispensers can roughly be divided into two types depending upon their manner of containing the powdery medicines.

The device of the first type may be a unit dosage dispenser or container in which a powdery medicine of an amount (unit dosage) that will be administered each time is contained in a suitable container as a unit, and is administered in an amount of a unit dosage for every administering operation. The device of the second type may be a multi-dosage dispenser or container in which a powdery medicine of an amount (multiple dosages) that will be administered a plural number of times is contained in a suitable container, and the powdery medicine of a unit dosage is correctly taken out from the container and is administered for every administration operation. Examples of the former unit dosage dispenser further include a simple device or a disposable container which also works as a disposable device that can be disposed of after each administration operation.

Unit dosage dispenser containers have been disclosed in Japanese Unexamined Patent Publication (Kokai) No. 59-34267 and Japanese Patent Publication (Kokoku) No. 63-6024. These devices are usually equipped with a unit dosage container-holding portion held in a capsule or the like, means for perforating the unit dosage container, and means for introducing the air stream to spray the powdery medicine from the perforated container into the nasal cavities or the like cavities of a patient. A disposable container has further been disclosed in Japanese Unexamined Patent Publication (Kohyo) No. 2-500172, according to which the powdery medicine dispenser container comprises a medicine-holding portion in which a fine powdery medicine is contained and of which the head portion has an opening for spraying or sucking the powdery medicine, and means for introducing the air, the bottom of the medicine-holding portion being communicated with the means for introducing the air through an air-permeable membrane but which does not permit the powdery medicine to pass through.

A multi-dosage dispenser container has been disclosed in, for example, WO94/26338.

According to this specification, the device comprises a device body, a storage chamber detachably mounted on said body and capable of storing a powdery medicine in an amount (multiple dosages) for plural times of administrations, medicine distribution means having a container chamber of a capacity (unit dosage) for each administration operation and is movably mounted on said body, so that said container chamber at a charging position is communicated with said storage chamber to administer the powdery medicine in the container chamber, means for moving said distribution means between the charging position and the administering position, and pump means for stirring the powdery medicine in the storage chamber by injecting the air into the storage chamber through the container chamber at the charging position, wherein the powdery medicine of a predetermined amount after stirring is charged into said container chamber from said storage chamber relying upon the suction force by said pump means and/or gravity.

As described above, many dispenser devices or containers have heretofore been devised accompanied, however, by their respective problems.

That is, the unit dosage dispenser disclosed in Japanese Unexamined Patent Publication (Kokai) No. 59-34267 and Japanese Patent Publication (Kokoku) No. 63-6024 must be equipped with means for perforating the medicine container. Therefore, the device becomes bulky and not suited for being carried. Besides, a cumbersome operation is required for putting the medicine container in the device and effecting the perforation for each administration operation, removing the container after the administration operation, and washing the device after it is used for extended periods of time.

The multi-dosage dispenser disclosed in the specification of WO94/26338 is constituted by a medicine storage unit, a medicine container chamber for each administration operation, means for measuring the medicine, and pump means. Therefore, the dispenser is considerably bulky and is not suited for being carried, and must be washed after it is used for extended periods of time.

The disposable container disclosed in Japanese Unexamined Patent Publication (Kohyo) No. 2-500172 is free from the problems of the above-mentioned multi-dosage device or the unit dosage device, but has a separator wall between the medicine-holding unit and the air introduction means. Therefore, the device is fabricated through complex fabrication steps, is likely to be broken during the pumping provided the separator wall is not strongly adhered to the periphery thereof, and becomes expensive due to the use of a filter as the separator wall, and is not economical if it is to be discarded after being used only once.

That is, none of the conventional powdery medicine dispensers or administering devices satisfy all of the requirements for being fabricated in small sizes so as to be easily carried, operated easily and quickly, fabricated through simple steps, fabricated using a small number of parts, and fabricated at low cost. In particular, when importance is given to portability, easy use and sanitation, it is strongly desired to provide a cheap and disposable administering device that can be fabricated through simple steps.

In order to solve the above-mentioned problems, the present inventors have studied the disposable container disclosed in Japanese Unexamined Patent Publication (Kohyo) No. 2-500172. That is, the inventors have removed the separator wall, contained the powdery medicine in the powdery medicine-holding portion which has an air reservoir that is formed together with the powdery medicine holding portion as a unitary structure, opened the head portion of the medicine-holding portion and depressed (pumped) the air reservoir in an attempt to spray the powdery medicine to the outside through the opening. In fact, however, though the medicine was partly sprayed, the medicine near the opening in the holding portion flew backwards when a negative pressure was created in the air reservoir, and all the medicine contained therein could not be sprayed. It was therefore learned that even when the powdery medicine is contained in a closed flexible container, the container is partly opened and is then pumped by being depressed in an attempt to spray and discharge the powdery medicine contained therein through the opening, the medicine flew backwards, and it was very difficult to spray and discharge all of the medicine.

In treating diseases in the nasal cavities, furthermore, the device for administering the powdery medicine must be capable of evenly spraying the powdery medicine into both nasal cavities.

To evenly spray and administer the medicine to both nasal cavities, there may be used two administering devices, one for one nasal cavity and another for another nasal cavity, or there may be used an administering device having two spray ports so that the medicine can be simultaneously administered into both nasal cavities. It can be further contrived to alternatingly spray and administer the powdery medicine into both nasal cavities by using a powdery medicine administering device having only one spray port, in order to evenly administer the medicine into both nasal cavities.

From the standpoint of portability, easy use and low cost, however, neither a method of using two administering devices nor the administering device having two spray ports is desired. It is desired to evenly administer the medicine into the nasal cavities by using only one administering device and by alternatingly spraying and administering the powdery medicine contained therein into both nasal cavities.

In order to evenly administer the powdery medicine into both nasal cavities by using only one powdery medicine administering device having only one spray port, the medicine may be administered into the nasal cavities in the order of, for example, right, left, left, right, . . . .

For this purpose, more than 90% of the medicine contained therein must by sprayed and discharged through the first four or six times of spraying, and the total amount of the powdery medicine sprayed in the first and fourth times must be equal to the total amount of the powdery medicine sprayed in the second and third times, or the total amount of the powdery medicine sprayed in the first, fourth and fifth times must be equal to the total amount of the powdery medicine sprayed in the second, third and sixth times.

DISCLOSURE OF THE INVENTION

In view of the problems and assignments inherent in the above-mentioned prior art, the present invention provides a device for administering a powdery medicine mentioned below.

That is, a first object of the present invention is to provide a device for administering a powdery medicine satisfying the requirements of portability, easy and quick operation, fabrication through simple steps, rigid structure, economy using decreased number of parts of low cost and/or constant-quantity spray performance.

A second object of the present invention is to provide a device for administering a powdery medicine which features excellent portability, and easy and quick operation, enabling a predetermined amount of the powdery medicine to be evenly administered to two diseased parts even through one spray port as in the case of treating a disease in the nasal cavities.

In order to accomplish the above-mentioned first object according to a first invention, there is provided a device for administering a powdery medicine comprising a medicine-holding portion having at least a partly flexible wall portion for defining therein a powdery medicine-container space which also serves as an air reservoir, and a medicine guide portion through which the space in said medicine-holding portion is communicated with the outside, wherein the space in said medicine-holding portion is communicated with the outside through said medicine guide portion only, said medicine guide portion is of a tubular structure having, at one end thereof, a medicine spray port at a position on the outside of said medicine-holding portion and having, at the other end thereof, a medicine suction port at a position in the space in said medicine-holding portion, the bottom of the space in said medicine-holding portion is positioned near and just under the medicine suction port of said medicine guide portion, said medicine suction port is disposed close to said bottom, and the powdery medicine is sprayed to the outside through said medicine guide portion upon depressing and relaxing the flexible wall portion of said medicine-holding portion.

The powdery medicine-container space in the medicine-holding portion contains a powdery medicine in an amount for one time of administration. The powdery medicine is accumulated on the bottom in the space, i.e., on a region close to the medicine suction port of the medicine guide portion. Upon depressing the flexible wall portion of the medicine-holding portion, the pressure in the space abruptly increases and the air contained therein starts flowing out through the medicine suction port of the medicine guide portion. At this moment, the powdery medicine is sucked through the medicine suction port, and is sprayed to the outside through the medicine spray port and is administered to the diseased part. Thereafter, the flexible wall portion of the medicine-holding portion is relaxed and, at this moment, the powdery medicine staying in the tubular medicine guide portion is reversely sucked by the space therein and is stirred together with the powdery medicine staying in the space therein. Upon repeating the above-mentioned operation, almost all of the powdery medicine is sprayed and discharged.

In order to accomplish the above-mentioned second object according to a second invention, furthermore, there is provided a device for administering a powdery medicine comprising a medicine-holding portion having at least partly flexible wall portion for defining an internal space of a shape for storing a predetermined amount of a powdery medicine in a bottom region, most of other regions serving as an air reservoir portion, and a medicine guide portion through which the space in said medicine-holding portion is communicated with the outside, wherein the space in said medicine-holding portion is communicated with the outside through said medicine guide portion only, said medicine guide portion is of a tubular structure having, at one end thereof, a medicine spray port at a position on the outside of said medicine-holding portion and having, at the other end thereof, a medicine suction port at a position in the space in said medicine-holding portion, the bottom of the space in said medicine-holding portion is positioned nearly just under the medicine suction port of said medicine guide portion, said medicine suction port is disposed close to said bottom, one or more slit(s) are formed in the side surfaces of said medicine guide portion of said tubular structure, said slits being continuous to, or close to, said medicine suction port, and the areas of said slits being not larger than two times the area of said medicine suction port, the upper surface of the powdery medicine is positioned on the upper side of said medicine suction port but on the lower side of the upper end of said slits, and the powdery medicine is sprayed to the outside through said medicine guide portion upon repetitively depressing and relaxing the flexible wall portion of said medicine-holding portion.

A predetermined amount of the powdery medicine (for one time of administration) is contained in the powdery medicine-container space in the medicine-holding portion as in the first invention. According to the second invention, however, the upper surface of the powdery medicine accumulated on the bottom of the space is positioned on the upper side of the medicine suction port but on the lower side of the upper end of the slits. Therefore, in spraying and discharging the powdery medicine to the outside by repetitively depressing and relaxing the flexible wall portion of the medicine-holding portion, the flow passage of the air is maintained at all times by the slits and, besides, the powdery medicine contained therein is involved in the air stream that is produced and is sprayed and discharged to the outside. Therefore, the medicine is sprayed in large amounts in the first time, and almost all the medicine is sprayed and discharged upon repeating the depression and relaxing several times. Accordingly, when used for treating disease in the nasal cavities, the powdery medicine can be administered to both the right and left nasal cavities evenly and repetitively as in right, left, left, right, . . .

DETAILED DESCRIPTION OF THE INVENTION

First, described below are the elements common to the first invention and to the second invention.

The device is used in a state where the medicine spray port is located on the upper side and the medicine suction port is located on the lower side, and the medicine-holding portion which also serves as the air reservoir is depressed from the sides and is relaxed, so that the powdery medicine contained in an amount for one time of administration is all sprayed and administered.

The wall portion of the medicine-holding portion is at least partly made of a flexible material.

Here, the wall portion that is at least partly made of a flexible material means that upon depressing and relaxing the portion made of the flexible material, the medicine-holding portion works as the air reservoir causing the powdery medicine contained in the medicine-holding portion to be sprayed and sucked. This may include the case where the whole medicine-holding portion is made of a flexible material and the case where the medicine-holding portion is made of a flexible material but the medicine guide portion, junction portion and the remaining portions are made of a non-flexible material.

Examples of the flexible material include plastic materials having plasticity such as polyethylene, polypropylene, etc., and natural and synthetic rubbers. Among them, it is desired to use plastic materials such as polyethylene, polypropylene, etc.

The size of the medicine-holding portion varies depending upon the amount of the powdery medicine that is contained and the sectional area of the medicine guide portion that will be described later, but should desirably hold the air in such an amount that the powdery medicine contained in the medicine-holding portion is almost all discharged upon depressing and relaxing the medicine-holding portion plural times. It is further desired that the medicine-holding portion holds the air in an amount which is enough for fluidizing and stirring the powdery medicine remaining in the medicine-holding portion to a sufficient degree upon one depressing operation.

From the standpoint of portability, the medicine-holding portion should not be too large and should desirably have a volume of not larger than 10 cm$^3$.

The medicine guide portion is of a tubular structure having a medicine spray port that can be opened or that is opened at an end on the outside of the medicine-holding portion and having a medicine suction port at the other end on the inside of the medicine-holding portion. Owing to this structure, the inside and the outside of the medicine-holding portion can be communicated with each other. That is, the inside of the medicine-holding portion is allowed to be communicated with the outside of the medicine-holding portion through the medicine guide portion only.

The medicine guide portion has a tubular shape such as circular shape, elliptic shape or the like shape without, however, any limitation on the cross-sectional shape thereof. When the medicine guide portion is of a tubular form having a circular shape in cross section for easy production, it is desired that the inner radius thereof is not larger than about 2 mm from such a standpoint that the amount for one time of dosage can be sprayed and administered being divided into plural times, though there is no particular limitation on the sectional area. The medicine guide portion may have the form of a straight pipe or may be curved within a range which does not impair the spraying, provided the above-mentioned conditions are satisfied.

The sectional area of the medicine guide portion must not be too broad. If it is too broad, a depression stroke is not obtained to a sufficient degree when the medicine-holding portion is depressed, and the flowing velocity of the air stream passing through the medicine suction port becomes too slow permitting the medicine to remain in the medicine-holding portion despite the medicine-holding portion being depressed and relaxed to spray and discharge the medicine. When the medicine guide portion is of a tubular form having a circular shape in cross section for easy production, it is desired that the outer radius thereof (outer radius at the portion of the medicine suction port) is not larger than about 4 mm.

The medicine guide portion may be made of a flexible material like the medicine-holding portion or may be made of another material. Among them, it is desired to use a flexible material such as polyethylene, polypropylene, etc. as for the medicine-holding portion.

The medicine guide portion is so disposed that the medicine suction port is close to the medicine-holding portion, so that the bottom of the medicine-holding portion is positioned near and just under the medicine suction port of the medicine guide portion. Upon depressing and relaxing the medicine-holding portion plural times, therefore, the powdery medicine contained in the medicine-holding portion is sucked through the medicine suction port of the medicine guide portion, and is sprayed or sucked from the inside of the medicine-holding portion to the outside thereof through the medicine spray port. Here, the medicine guide portion must be located close to the medicine-holding portion.

This is because, if the distance is large, the medicine in the medicine-holding portion is not sucked through the suction port of the medicine guide portion despite the medicine-holding portion being repetitively depressed and relaxed. The closest distance between the medicine guide portion and the medicine-holding portion varies depending upon the volume of the medicine-holding portion, inner diameter of the medicine guide portion, amount of the powdery medicine contained in the medicine-holding portion, specific gravity of the medicine, etc.

To spray all of the powdery medicine without leaving any of it, it is desired that the distance is not larger than 5 mm from such a standpoint that the size of the medicine-holding portion which is convenient for being carried is not larger than 10 cm$^3$ in terms of the volume, the powdery medicine which is usually used has an apparent specific gravity of about 0.1 to 3.0, and the amount of the powdery medicine that is contained for one time of administration (equal to the amount sprayed) is about 5 to 200 mg.

The medicine guide portion is inserted in the medicine-holding portion through an opening that fits to the medicine guide portion in cross section and is formed in the outer part of the medicine-holding portion on the side opposite to the bottom. The medicine guide portion is then melt-adhered, forcibly inserted, or is fitted to a screw that has been threaded in advance. Thus, the medicine guide portion and the medicine-holding portion are joined together as a unitary structure. In this case, the medicine guide portion may be joined to the medicine-holding portion in a manner that the medicine spray port formed at one end of the medicine guide portion exists flush with the surface of the medicine-holding portion, or that the medicine spray port protrudes beyond the outer surface of the medicine-holding portion. When the powdery medicine is to be sprayed and administered into body cavities of relatively limited areas such as nasal cavities, it is desired that the medicine spray port is outwardly protruded beyond the medicine-holding portion.

The medicine spray port of the medicine guide portion is so constituted that an opening is formed upon wrenching off a knob formed at the head portion thereof. Otherwise, a closure may be attached by a suitable means so that the medicine will not leak when it is not in use, and the closure is removed to communicate the outside with the inside to use the medicine. Such a closure may be of the type that is fitted to the medicine spray port, of the type that is fitted like a plug, or of a screw type.

To use the thus obtained administering device of the present invention, the knob formed at the head of the medicine guide portion is wrenched off to open the medicine spray port or the closure is removed, the medicine-holding portion is depressed and relaxed several times so that the powdery medicine is fluidized and stirred in the medicine-holding portion and is sprayed and discharged in almost all amount, and is sprayed and administered to the diseased part.

Next, described below are matters specific to the above-mentioned first invention without a slit in the medicine guide portion.

In order to store a predetermined trace amount of the powdery medicine (for one time of administration) on the bottom region in a concentrated manner, it is desired that the medicine-holding portion has a bottom which is not flat but is elliptic extending up and down, oval or is of the shape of an eggplant, or is of a spherical shape or of the shape of a pear. However, the bottom may be flat and the medicine-holding portion may have the shape of a cylinder or a drum provided the medicine can be stored in a concentrated manner.

When the medicine-holding portion has a cylindrical shape and when the bottom of the medicine-holding portion facing the medicine suction port has a flat surface, the bottom having a wide area permits the medicine to stay in the medicine-holding portion despite attempts to spray and discharge the medicine by depressing and relaxing the medicine-holding portion. Therefore, the area of the flat bottom of the medicine-holding portion relative to the medicine suction port is limited to within a range in which the medicine does not stay. In dealing, for example, with an ordinary powdery medicine, it is desired that a relation $R<5r$ is maintained where r is a radius of a circle of the medicine suction port in cross section and R is a radius of a circle of the bottom of the medicine-holding portion.

It is desired that the medicine spray port and the medicine suction port are formed in a number of one, respectively, since it makes it possible to spray or suction-administer almost all the powdery medicine contained in the medicine-holding portion without leaving any. When the powdery medicine is to be sprayed and administered into the nasal cavities, however, the medicine spray port may be formed only at one place or may be branched into a plurality of ports such as two ports near the medicine spray port, i.e., a total of two medicine spray ports may be formed at the ends to meet the purpose.

Such an administering device of the first invention is capable of spraying almost all the powdery medicine, and is suited for administering the medicine into body cavities and, particularly, into nasal cavities and oral cavity. The medicine may be the one that acts on the whole body or on a local part of the body.

Next, described below are matters specific to the above-mentioned second invention having slits formed in the medicine guide portion.

In order to store a predetermined trace amount of the powdery medicine (for one time of administration) on the bottom region in a concentrated manner, it is desired that the medicine-holding portion has a bottom which is not flat but is elliptic extending up and down, oval or of the shape of an eggplant, or is of a spherical shape or of the shape of a pear. However, the bottom may be flat and the medicine-holding portion may have the shape of a cylinder or a drum provided the medicine can be stored in a concentrated manner.

Slits are formed continuous to, or close to, the suction port in the side surfaces along the axis of the medicine guide portion. Even when the upper surface of the powdery medicine contained in the medicine-holding portion is higher than the medicine suction port of the medicine guide portion, therefore, the horizontal surface of the powdery medicine contained in the medicine-holding portion is located to be lower than the upper end of the slits. Upon repetitively depressing and relaxing the medicine-holding portion, therefore, the air flow passage is maintained at all times for spraying and discharging the powdery medicine in the medicine-holding portion to the outside. Moreover, the powdery medicine contained therein is involved in the air stream that is created, and is sprayed and discharged to the outside. Therefore, the medicine is not sprayed in too large an amount the first time. Besides, almost all the medicine that is contained is sprayed and discharged and can be evenly sprayed and administered to both nasal cavities.

There is no particular limitation in the shape of the slits. By taking the moldability at the time of production into consideration, however, it is desired to form the slits in a rectangular shape or in a triangular shape in the side surfaces of the medicine guide portion, the slits being continuous to the suction port in a direction in parallel with the axis.

The areas of the slits must not be too large. When the slits have wide areas, the velocity of the air stream decreases when the medicine-holding portion is repetitively depressed and relaxed to spray and discharge the powdery medicine in the medicine-holding portion to the outside; i.e., the powdery medicine contained therein is less involved in the air stream and is less sprayed and discharged to the outside, making it difficult to spray and discharge the powdery medicine contained in the medicine-holding portion in all amounts. By taking the fact that the medicine-holding portion has a volume of not larger than 10 cm$^3$ into consideration, it is desired that the slits have areas of not more than two times the area of the suction port.

The height of the slits must be such that the horizontal surface of the powdery medicine contained in the medicine-holding portion is lower than the upper end of the slits, and is desirably from 2 to 10 mm from such a standpoint that the powdery medicine that is usually used has an apparent specific gravity of about 0.1 to 3.0 and the amount of the powdery medicine contained for one time of administration is about 5 to 200 mg.

The slits must not be too wide. It is desired that the slits that are formed have areas which are not larger than two times the area of the suction port and have a height of 2 to 10 mm. Therefore, when the slits are formed on both sides and have an elongated shape, it is desired that their width is 0.1 to 1 mm.

The slits may be formed in any number but should have areas which are not larger than two times the area of the suction port. It is desired that the slits are formed at one to four places from the standpoint of producing the device with high precision.

To use the thus produced device for administering the powdery nasal medicine of the second invention, a knob is wrenched off to open the medicine spray port, and the medicine-holding portion is depressed and relaxed to spray and administer the powdery nasal medicine alternatingly into both nasal cavities. Thus, the powdery nasal medicine can be evenly administered to both nasal cavities.

The slits formed in the side surfaces along the axis of the medicine guide portion are not used as other medicine suction ports. The object of the slits is to maintain the air-flow passage at all times when the powdery medicine in the medicine-holding portion is to be sprayed and discharged to the outside by repetitively depressing and relaxing the medicine-holding portion, so that the powdery medicine contained therein is involved in the air stream that is created and is sprayed and discharged to the outside.

When another small medicine suction port of a circular shape or the like shape is formed in the side surface along the axis of the medicine guide portion, the discharge resistance becomes so small that the powdery medicine contained therein is not involved in the air stream that is created and is not sprayed and discharged to the outside.

That is, the slits so work that the powdery medicine is involved in the air stream, which is different from the effect of when the medicine suction ports are formed simply in an increased number.

Such an administering device of the second invention is capable of spraying almost all the powdery medicine into both nasal cavities nearly evenly, and is suited for administering the medicine into nasal cavities. The medicine may particularly be the one that acts on a local part of the body but may also be the one that acts on the whole body.

Here, attention should be given so that even when a liquid medicine in an amount of one time of administration is contained in the administering devices of the first and second inventions, the liquid medicine is scarcely sprayed and discharged.

That is, even when the liquid medicine of an amount of one time of administration such as an aqueous preparation of an amount of about 0.1 ml is contained and the medicine-holding portion is repetitively depressed and relaxed, the aqueous preparation scatters onto the surfaces of the medicine-holding portion due to the air that flows reversely and adheres to the scattered portions. Despite repeated depression and relaxing, the aqueous preparation does not fall on a portion near the medicine suction port of the guide portion, and about 0.05 ml of the aqueous preparation remains in the container without being sprayed and discharged. A liquid medicine administering device has been known containing a liquid medicine in an amount of many times of administration in the medicine-holding portion. Even when the liquid medicine of an amount of one time of administration is contained in such a known liquid medicine administering device, however, the device for administering the medicine at one time is not realized.

As described above, the administering devices of the first and second inventions are convenient to carry, easy to operate, can be quickly discarded after the use, have a rigid structure, and can be produced relatively cheaply. In particular, the devices are suited for containing a powdery medicine in a small amount for one time of use.

BRIEF DESCRIPTION OF DRAWINGS

The devices for administering a powdery medicine according to the first and second inventions will now be described by way of embodiments with reference to the accompanying drawings, therein:

FIGS. 6(a) to 6(c) illustrating the administering device of the embodiment 3 where the width and length of the slits are specified.

EMBODIMENTS

Figure 1:
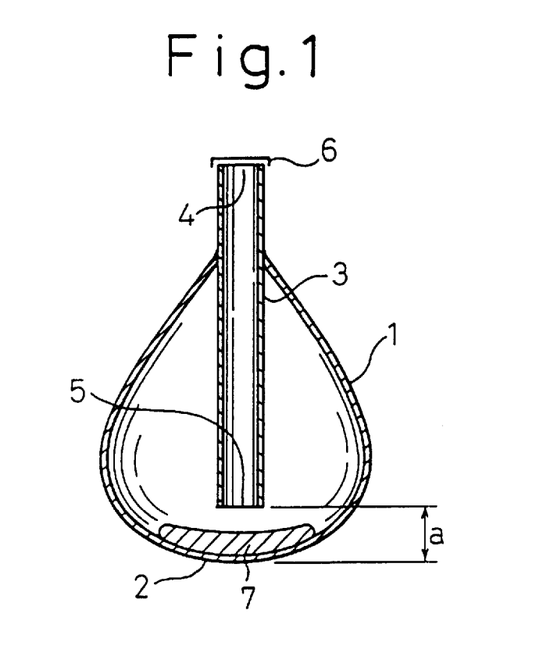
FIG. 1 is a sectional view illustrating the constitution of an administering device (without slit) according to an embodiment 1.

FIG. 1 is a sectional view illustrating the whole constitution of an administering device in which the medicine-holding portion is in the shape of an eggplant according to an embodiment 1. The medicine-holding portion 1 in the shape of an eggplant of a circular shape of a radius of 2 mm having an opening formed at one place, is obtained by molding polyethylene. A powdery medicine 7 of an amount of 20 mg for one time administration is charged into the medicine-holding portion 1 through the opening by using a trace-amount-of-powder charging machine. Then, a straight tubular medicine guide portion 3 made of a polyethylene is inserted in the opening of the medicine-holding portion. The medicine guide portion has a circular shape in cross section, the inner radius being 1 mm and the outer radius being 2 mm. The distance a from the medicine suction port 5 in the medicine guide portion to the bottom 2 of the medicine-holding portion is 3 mm. The medicine guide portion and the opening of the medicine-holding portion are joined together by heating and melting small areas where they are in contact with each other. Then, a cap 6 is intimately fitted to a medicine spray port 4 of the medicine guide portion to obtain the administering device of the embodiment 1.

Figure 2:
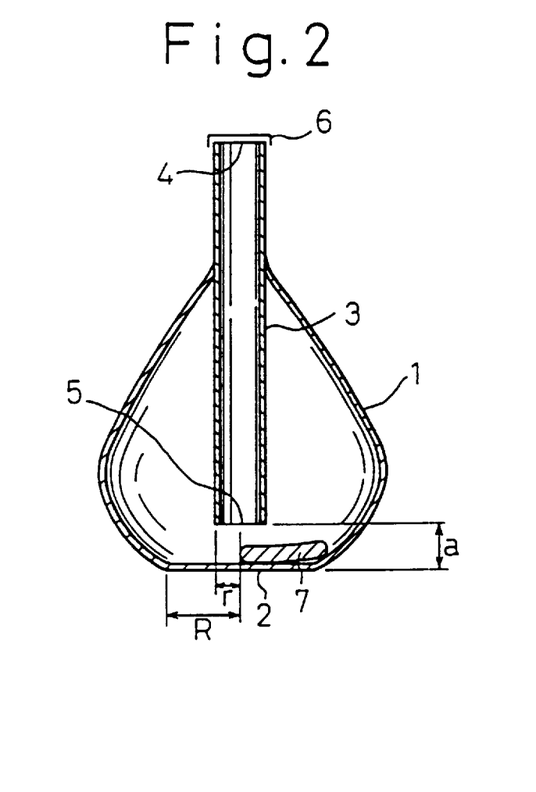
FIG. 2 is a sectional view illustrating the constitution of an administering device (without slit) according to an embodiment 2.

FIG. 2 illustrates an administering device of an embodiment 2 in which the bottom of the medicine-holding portion 1 is of a circular flat plane of a radius R. The medicine-holding portion 1 of the type of an eggplant is obtained by molding polyethylene, the medicine-holding portion having an opening of a circular shape of a radius of 2 mm and having the bottom of a flat shape. A powdery medicine 7 of an amount of 20 mg for one time of administration is charged into the medicine-holding portion 1 through the opening by using a trace-amount-of-powder charging machine. Then, a straight tubular medicine guide portion 3 made of a polyethylene is inserted in the opening of the medicine-holding portion. The medicine guide portion has a circular shape in cross section, the inner radius being 1 mm and the outer radius being 2 mm. The distance a from the medicine suction port 5 in the medicine guide portion to the bottom 2 of the medicine-holding portion is 3 mm. The medicine guide portion and the opening of the medicine-holding portion are joined together by heating and melting small areas where they are in contact with each other. Then, a cap 6 is intimately fitted to a medicine spray port 4 of the medicine guide portion to obtain the administering device of the embodiment 2.

Figure 3A:
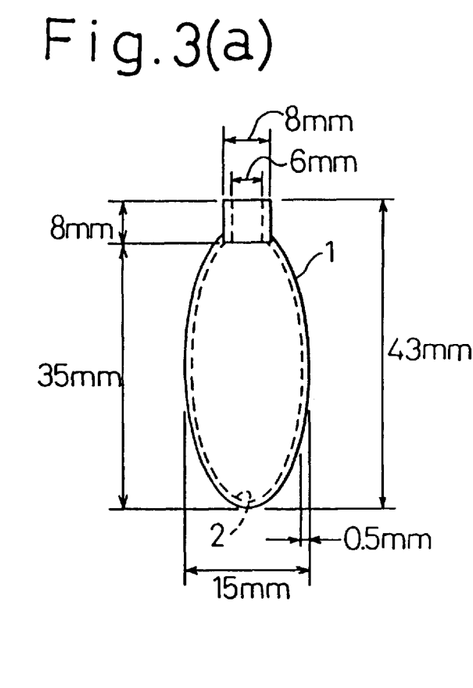
FIGS. 3(a) to 3(c) are diagrams illustrating the constitution of an administering device (with slits) according to an embodiment 3, wherein the diagram (a) illustrates a main body or a medicine-holding portion, the diagram (b) illustrates a medicine guide portion, and the diagram (c) illustrates a suction port on an enlarged scale.
Figure 3B:
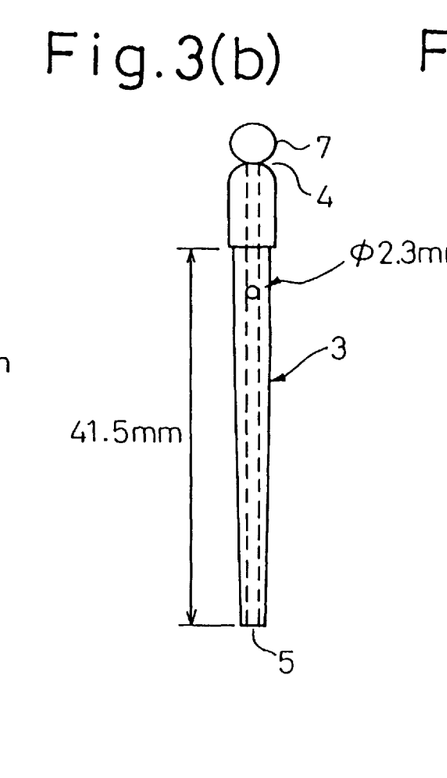
Figure 3C:
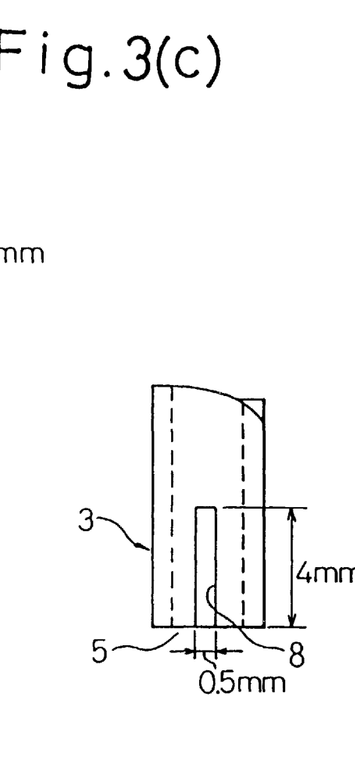

FIG. 3 illustrates an administering device of an embodiment 3 in which the medicine-holding portion has an elliptic shape extending up and down. FIG. 3(a) shows a medicine-holding portion 1 obtained by molding polyethylene and having a volume of about 10 cm$^3$ and having a neck of a length of 8 mm with a circular opening of a radius of 3 mm formed in an upper portion thereof, the medicine-holding portion 1 being of an elliptic shape or a shape of a Rugby ball which is elongated up and down. The medicine-holding portion 1 has a thickness of about 0.5 mm in the main body thereof and about 1 mm in the neck thereof. The main body can be easily depressed by hand due to its resiliency and relaxes to assume its initial state owing to a resilient restoring force. FIG. 3(b) shows a straight tubular medicine guide portion 3 obtained by molding polypropylene and having a knob 7 that can be wrenched off at the head portion thereof and a medicine discharge passage of an inner diameter of 2.3 mm extending from a medicine spray port 4 to a suction port 5. As shown in FIG. 3(c), slits 8 continuous to the suction port 5 are formed on both sides of the suction port 5 of the medicine guide portion 3. 30 Milligrams of Rhinocort (trade name) which is a powdery medicine before being encapsulated is charged into the medicine-holding portion 1 through the opening thereof, and the medicine guide portion 3 is forcibly inserted in the opening of the medicine-holding portion 1 to obtain the administering device of the embodiment 3. The device has sizes as shown, and the gap between the intake port 5 and the inner bottom 2 is about 2 mm.

Figure 4:
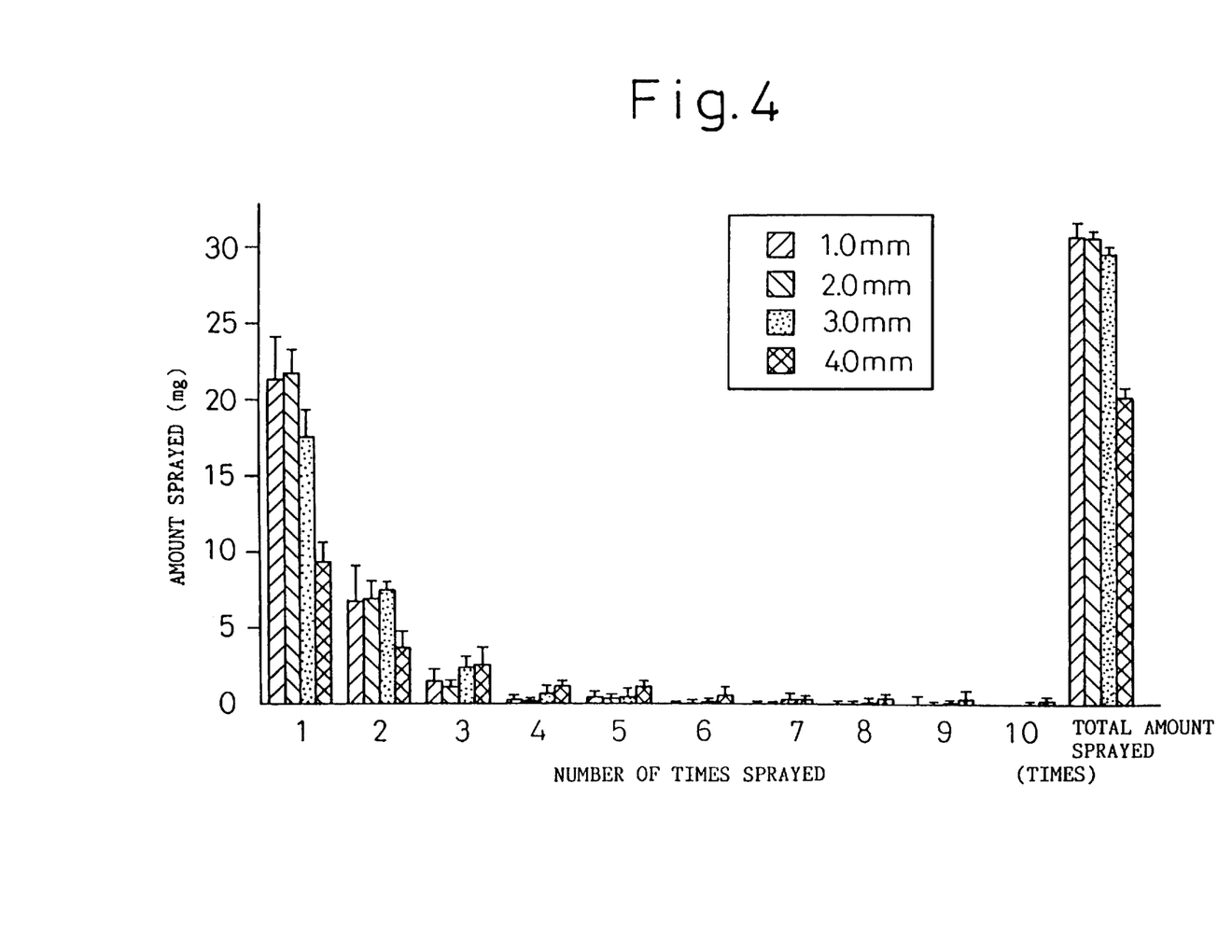
FIG. 4 is a diagram illustrating the distribution of the amounts sprayed of when the administering device having nearly the same shape as that of the embodiment 3, but without a slit, is used.

FIG. 4 illustrates the measurement of the amounts sprayed of when the administering device having nearly the same shape as that of the embodiment 3 but without a slit is used. Four kinds of the devices are prepared having gaps of 1 mm, 2 mm, 3 mm and 4 mm between the suction port 5 of the medicine guide portion 3 and the inner bottom of the medicine-holding portion 1. 30 Milligrams of Rhinocort (trade name) which is a powdery medicine of before being encapsulated is charged into each of the devices. The height of the powdery medicine from the inner bottom is 3.5 mm. Each device is depressed and relaxed repetitively ten times. Each time, the bottom of the device is slightly struck onto the table to collect the powdery medicine in the lower portion of the medicine-holding portion 1. The abscissa represents the number of times of depression and relaxation, and the ordinate represents the amount of the powdery medicine sprayed each time. It is learned that when the gap between the suction port 5 and the inner bottom 2 is 4 mm, the medicine is not all sprayed even after the depression and relaxation are repeated 10 times. When the gap is 1 to 3 mm, about two-thirds of the medicine is sprayed the first time.

By using the administering devices without a slit 8 as described above, the medicine is sprayed in large amounts the first time, i.e., more than one-half of the medicine contained therein is sprayed the first time. By using a portable and disposable medicine administering device having only one spray port for treating disease in the nasal cavities, therefore, it is not possible to evenly administer the medicine into both nasal cavities. By using the administering device having slits 8 as described below, on the other hand, the medicine is sprayed in a reduced amount the first time, and almost all is sprayed after it is depressed and relaxed several times, making it possible to uniformly administer the medicine into both nasal cavities.

Figure 5A:
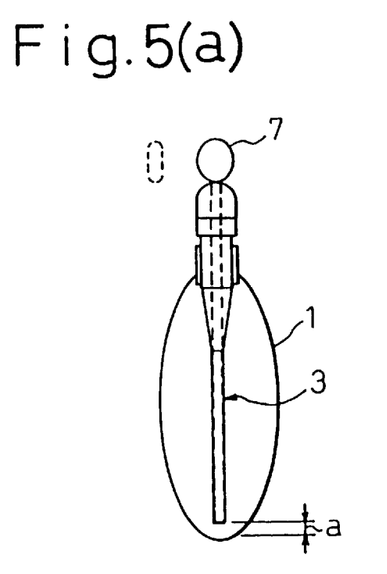
FIGS. 5(a) to 5(c) are diagrams illustrating the constitution of an administering device (with slits) according to an embodiment 4, wherein the diagram (a) illustrates the whole constitution, the diagram (b) illustrates the medicine guide portion, and the diagram (c) illustrates the suction port on an enlarged scale.
Figure 5B:
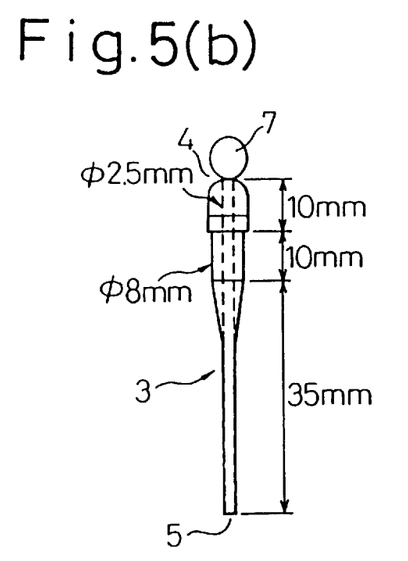
Figure 5C:
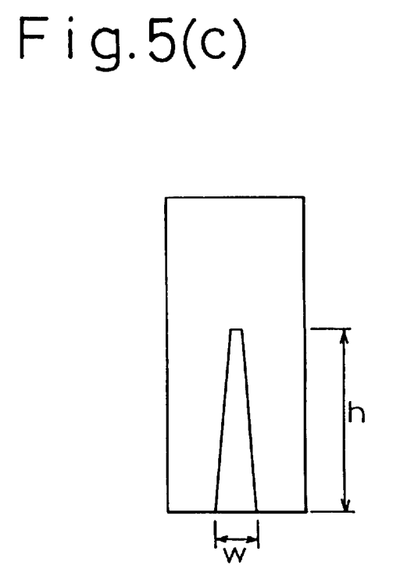

FIGS. 5(a) to 5(b) illustrate an administering device of an embodiment 4 prepared to examine a change in the amount of spraying the medicine of when the slits 8 are formed in various sizes, wherein FIG. 5(a) illustrates a state where the medicine guide portion 3 is forcibly inserted in the medicine-holding unit 1 having the size and shape same as those of the embodiment 3 and obtained by molding polyethylene. FIG. 5(b) illustrates a straight tubular medicine guide portion 3 obtained by molding polypropylene and having a medicine discharge passage of an inner diameter of 2.5 mm from the spray port 4 to the intake port 5 and further having at the head portion thereof a knob 7 that can be wrenched away to form a spray port 4. Referring to FIG. 5(c), the slits 8 formed on both sides of the suction port 5 of the medicine guide portion 3 have triangular shapes, the bottom side or the width (W) being 1 mm and 2 mm, and the height (h) being 2 mm, 3 mm, 4 mm and 5 mm. 30 Milligrams of Rhinocort (trade name), which is a powdery medicine before being encapsulated, is charged into the devices to execute the spray testing. Furthermore, the gap between the intake port 5 and the inner bottom 2 is selected to be 1 mm and 2 mm. Each time after the medicine is sprayed, the bottom of the device is slightly struck to the table to collect the powdery medicine in the lower portion of the medicine-holding portion 1. In the fifth, sixth and seventh times and in the eighth, ninth and tenth times, however, the medicine is continually sprayed to make sure whether the powdery medicine is sprayed in all amount or not. The following tables show the results of when the medicine is sprayed 10 times using these devices.

| (1) Distance from the bottom: | 1 mm | | | |
|---|---|---|---|---|
| Width of slit: | 1 mm | | | |
| Length of slit | 1 mm | 2 mm | 3 mm | 4 mm |
| Area of slit | 1 mm$^2$ | 2 mm$^2$ | 3 mm$^2$ | 4 mm$^2$ |
| Amount charged (mg) | 30.20 | 30.30 | 30.32 | 30.32 |
| Amount sprayed (mg) | 28.46 | 28.56 | 28.04 | 26.36 |
| Spraying factor (%) | 94.24 | 94.26 | 92.48 | 86.94 |

| | -continued | | | |
|---|---|---|---|---|
| (2) Distance from the bottom: Width of slit: | | 1 mm 2 mm | | |
| Length of slit | 1 mm | 2 mm | 3 mm | 4 mm |
| Area of slit | 2 mm² | 4 mm² | 6 mm² | 8 mm² |
| Amount charged (mg) | 30.50 | 30.38 | 30.20 | 30.48 |
| Amount sprayed (mg) | 28.38 | 26.62 | 23.66 | 19.82 |
| Spraying factor (%) | 93.05 | 87.62 | 78.34 | 65.03 |

As will be obvious from the above results, the medicine can be sprayed in a total amount of not smaller than 85% when the area of the slits 8 (total area of the two slits) is equal to, or smaller than, the area of the medicine suction port (having an inner diameter of 2.5 mm and an area of about 4 cm²). As described above, not all the powdery medicine is sprayed when the slits 8 have too large an area.

Figure 6A:
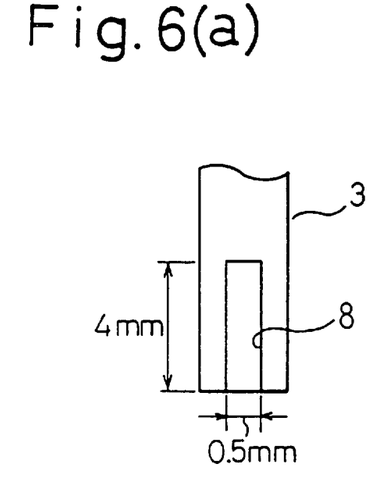
Figure 6B:
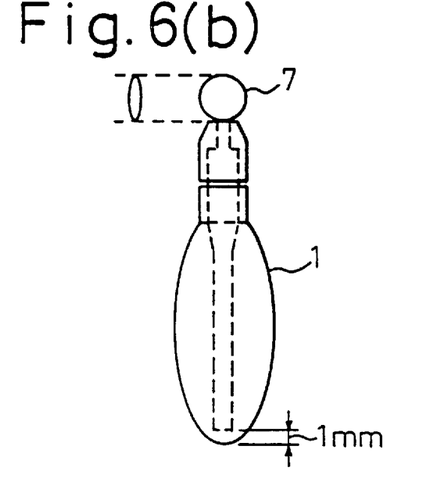

FIG. 6 shows an administering device of the embodiment 3 but in which the slits 8 formed on both sides of the suction port 5 of the medicine guide portion 3 have a rectangular shape, are continuous from the suction port 5 and have a width of 0.5 mm and a height of 4 mm. The medicine guide portion 3 has an inner diameter of 1.3 mm at the spray port 4 and 2.5 mm at the suction port 5. Furthermore, the medicine discharge passage has an inner diameter of 2.5 mm. About 30 milligrams of Rhinocort (trade name), which is a powder medicine before being encapsulated, is charged to execute the spray testing. The gap between the suction port 5 and the inner bottom 2 is 1 mm. After each spraying is executed ten times, the bottom of the administering device is slightly struck to the table to collect the powdery medicine in the bottom portion of the medicine-holding portion. The measured results of the amounts sprayed are as tabulated below.

Figure 7:
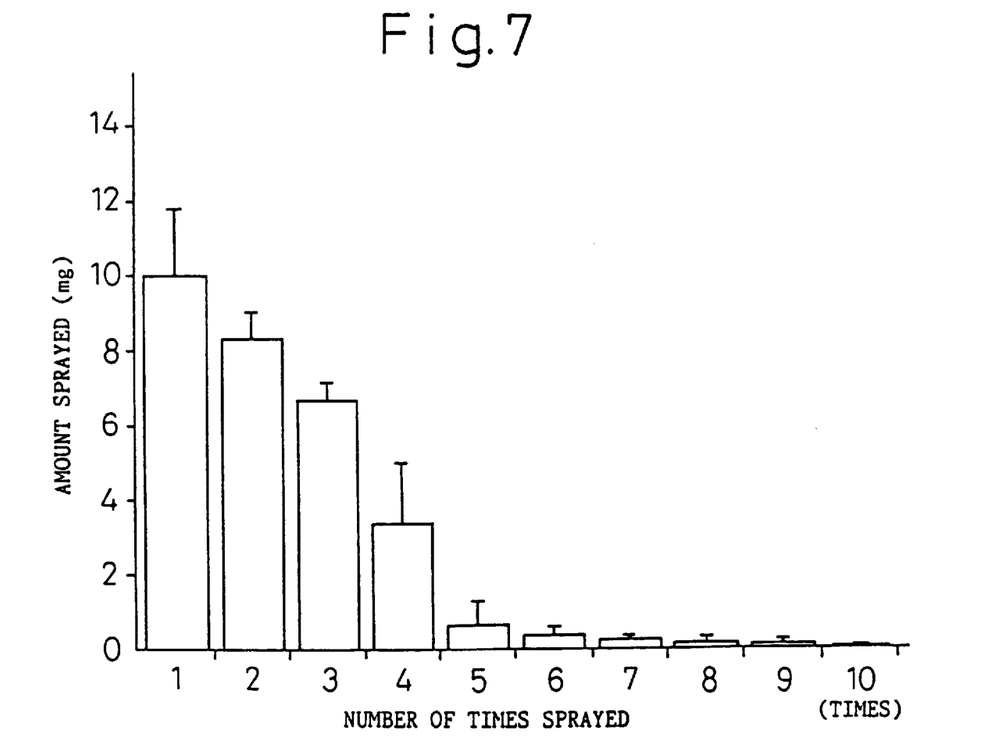
FIG. 7 is a diagram illustrating the distribution of the amounts sprayed when slits are formed as shown in FIG. 6.

| Amount charged (mg) | 30.18 ± 0.15 |
|---|---|
| Sprayed amount, 1st time | 9.98 ± 1.81 |
| Sprayed amount, 2nd time | 8.30 ± 0.73 |
| Sprayed amount, 3rd time | 6.66 ± 0.49 |
| Sprayed amount, fourth time | 3.36 ± 1.64 |
| Sprayed amount, fifth time | 0.64 ± 0.63 |
| Sprayed amount, sixth time | 0.36 ± 0.22 |
| Sprayed amount, seventh time | 0.24 ± 0.11 |
| Sprayed amount, eighth time | 0.14 ± 0.19 |
| Sprayed amount, ninth time | 0.12 ± 0.13 |
| Sprayed amount, tenth time | 0.04 ± 0.05 |
| Total | 29.84 ± 0.44 |
| Spraying factor | 98.90% |
| Total amount sprayed after tenth time | 29.84 mg (98.9% of the charged amount) |
| Total amount sprayed after 1st, 4-th, 5-th, 8-th and 9-th times | 14.24 mg (47.2% of the charged amount) |
| Total amount sprayed after 2nd, 3rd, 6-th, 7-th and 10-th times | 15.60 mg (51.7% of the charged amount) |
| Total amount sprayed after sixth time | 29.30 mg (97.1% of the charged amount) |
| Total amount sprayed after 1st, 4-th, and 5-th times | 13.98 mg (46.3% of the charged amount) |
| Total amount sprayed after 2nd, 3rd, and 6-th times | 15.32 mg (50.8% of the charged amount) |
| Total amount sprayed after fourth time | 28.30 mg (93.8% of the charged amount) |
| Total amount sprayed after 1st and 4-th times | 13.34 mg (44.2% of the charged amount) |
| Total amount sprayed after 2nd and 3rd times | 14.96 mg (49.6% of the charged amount) |

As will be obvious from the above results, formation of the slits 8 makes it possible to suppress the amount of the medicine sprayed in the first time to be about 30% of the total amount, and almost all the medicine is sprayed after several times of spraying. When applied to, for example, nasal catarrh, the medicine can be repetitively administered into the right and left nasal cavities like right, left, left, right, right, left, . . . so that the medicine can be evenly administered into both nasal cavities.

We claim:

1. A device for administering a powdery medicine comprising a medicine-holding portion having at least a partly flexible wall portion for defining therein a powdery medicine-container space which also serves as an air reservoir, and a medicine guide portion through which the space in said medicine-holding portion is communicated with the outside, wherein:

the space in said medicine-holding portion is communicated with the outside through said medicine guide portion only;

said medicine guide portion is of a tubular structure having, at one end thereof, a medicine spray port at a position on the outside of said medicine-holding portion and having, at the other end thereof, a medicine suction port at a position in the space in said medicine-holding portion; and the bottom of the space in said medicine-holding portion is positioned under the medicine suction port of said medicine guide portion, and said medicine suction port is spaced 1–4 mm from said bottom;

whereby the powdery medicine is sprayed to the outside through said medicine guide portion upon depressing and relaxing the flexible wall portion of said medicine-holding portion.

2. A device for administering a powdery medicine according to claim 1, wherein said medicine-holding portion has a spherical shape, elliptic shape, cylindrical shape, oval shape or the shape of an eggplant or a pear, to store a predetermined amount of the powdery medicine in the bottom portion thereof and to define an internal space which is the air reservoir in most of another portion.

3. A device for administering a powdery medicine according to claim 2, wherein said medicine-holding portion has a symmetrical shape, and said flexible wall portion is formed on at least both sides.

4. A device for administering a powdery medicine according to claim 1, wherein said medicine guide portion has a linear tubular structure.

5. A device for administering a powdery medicine according to claim 1, wherein the space in said medicine-holding portion has a volume of not larger than 10 cm³.

6. A device for administering a powdery medicine according to claim 1, wherein the medicine spray port of said medicine guide portion protrudes toward the outside of said medicine-holding portion.

7. A device for administering a powdery medicine according to claim 1, wherein said medicine guide portion is made of a plastic material, and said medicine spray port in said medicine guide portion is formed upon wrenching off a knob that is formed at the head portion of said medicine guide portion and formed of a plastic material integrally with said medicine guide portion.

8. A device for administering a powdery medicine according to claim 1, wherein said medicine spray port of said medicine guide portion is equipped with a closure that is detachably attached.

9. A device for administering a powdery medicine according to claim 1, wherein said device is used for administering medicine into nasal cavities or into an oral cavity.

10. A device for administering a powdery medicine comprising a medicine-holding portion having at least a partly flexible wall portion for defining an internal space of a shape for storing a predetermined amount of a powdery medicine on a bottom portion, most of another portion serving as an air reservoir portion, and a medicine guide portion through which the space in said medicine-holding portion is communicated with the outside, wherein:

the space in said medicine-holding portion is communicated with the outside through said medicine guide portion only;

said medicine guide portion is of a tubular structure having, at one end thereof, a medicine spray port at a position on the outside of said medicine-holding portion and having, at the other end thereof, a medicine suction port at a position in the space in said medicine-holding portion;

the bottom of the space in said medicine-holding portion is positioned under the medicine suction port of said medicine guide portion, and said medicine suction port is spaced 1–4 mm from said bottom; and one or more slit(s) are formed in the side surfaces of said medicine guide portion of said tubular structure, said slits being contiguous to, or close to, said medicine suction port, and the areas of said slits being not larger than two times the area of said medicine suction port, the upper surface of the powdery medicine is positioned on the upper side of said medicine suction port but on the lower side of the upper end of said slits;

whereby the powdery medicine is sprayed to the outside through said medicine guide portion upon repetitively depressing and relaxing the flexible wall portion of said medicine-holding portion.

11. A device for administering a powdery medicine according to claim 10, wherein said medicine-holding portion has a spherical shape, elliptic shape, cylindrical shape, oval shape or the shape of an eggplant or a pear, or the like shape.

12. A device for administering a powdery medicine according to claim 11, wherein said medicine-holding portion has a symmetrical shape, and said flexible wall portion is formed on at least both sides.

13. A device for administering a powdery medicine according to claim 10, wherein said medicine guide portion has a linear tubular structure.

14. A device for administering a powdery medicine according to claim 10, wherein said slits are formed at two places symmetrical with respect to the axis of the medicine guide portion of the tubular structure, and the total area of these two slits is not larger than two times the area of said medicine suction port.

15. A device for administering a powdery medicine according to claim 10, wherein the space in said medicine-holding portion has a volume of not larger than 10 cm$^3$.

16. A device for administering a powdery medicine according to claim 10, wherein the medicine spray port of said medicine guide portion protrudes toward the outside of said medicine-holding portion.

17. A device for administering a powdery medicine according to claim 10, wherein said medicine guide portion is made of a plastic material, and said medicine spray port in said medicine guide portion is formed upon wrenching off a knob that is formed at the head portion of said medicine guide portion and formed of a plastic material integrally with said medicine guide portion.

18. A device for administering a powdery medicine according to claim 10, wherein said medicine spray port of said medicine guide portion is equipped with a closure that is detachably attached.

19. A device for administering a powdery medicine according to claim 10, wherein said device is used for administering medicine into nasal cavities.

* * * * *